United States Patent [19]

Yasushi

[11] Patent Number: 5,495,853
[45] Date of Patent: Mar. 5, 1996

[54] SYSTEM FOR EVOKING ELECTROENCEPHALOGRAM SIGNALS

[75] Inventor: Mitsuo Yasushi, Kawagoe, Japan

[73] Assignee: Pioneer Electronic Corporation, Tokyo, Japan

[21] Appl. No.: 305,755

[22] Filed: Sep. 14, 1994

Related U.S. Application Data

[63] Continuation of Ser. No. 498,671, Mar. 26, 1990, abandoned.

[30] Foreign Application Priority Data

Aug. 10, 1989 [JP] Japan ..................... 1-205780

[51] Int. Cl.$^6$ .................................................. A61B 5/04
[52] U.S. Cl. .............................................. 128/732; 600/27
[58] Field of Search ................................. 128/731–732; 600/26–28

[56] References Cited

U.S. PATENT DOCUMENTS

| | | | |
|---|---|---|---|
| 3,255,753 | 6/1966 | Wing | 600/26 |
| 3,388,699 | 6/1968 | Webb | 600/26 |
| 3,753,433 | 8/1973 | Bakerich et al. | 128/732 |
| 3,837,331 | 9/1974 | Ross . | |
| 3,882,850 | 5/1975 | Bailin et al. | 128/732 |
| 3,893,450 | 7/1975 | Ertl . | |
| 3,896,790 | 7/1975 | Dikmen | 128/732 |
| 4,227,516 | 10/1980 | Meland et al. . | |
| 4,228,807 | 10/1980 | Yagi et al. . | |
| 4,315,502 | 2/1982 | Gorges | 600/27 |
| 4,462,411 | 7/1984 | Rickards . | |
| 4,595,013 | 7/1986 | Jones et al. | 128/644 |
| 4,697,598 | 10/1987 | Bernard et al. | 128/644 |
| 4,777,937 | 10/1988 | Rush et al. | 600/27 |
| 4,858,609 | 8/1989 | Cole | 600/26 |
| 4,902,274 | 2/1990 | Gleeson, III | 600/27 |
| 5,036,858 | 8/1991 | Carter et al. | 600/27 |
| 5,241,967 | 9/1993 | Yasushi et al. | 128/732 |
| 5,356,368 | 10/1994 | Monroe | 128/732 |

Primary Examiner—Angela D. Sykes
Assistant Examiner—Robert L. Nasser, Jr.
Attorney, Agent, or Firm—Sughrue, Mion, Zinn, Macpeak & Seas

[57] ABSTRACT

A system for evoking an electroencephalogram (EEG) signal from the brain of a user has a brain wave evoking terminal unit which includes a headgear for being mounted on the head of the user, a light emitter, mounted on the headgear, for applying an EEG signal evoking photic stimulus to the eyes of the user, and electrodes, mounted on the headgear, for detecting brain waves produced by the user. The system also has a brain wave signal processor, responsive to brain wave signals from the electrodes, for generating a stimulating signal having a frequency corresponding to a brain wave to be evoked, and for applying the stimulating signal to the light emitter. The brain wave to be evoked is extracted and fed back as stimulating light to the user, who can be rapidly and strongly brought into a desired brain wave condition. The brain wave signal processor may be combined with the brain wave evoking terminal unit, so that the system is small in size, simple in arrangement, and can be carried and mounted on the user's head with ease.

5 Claims, 5 Drawing Sheets

FIG. 1

FIG. 2 (A) EEG

FIG. 2 (B) PHOTIC STIMULUS SIGNAL $T_0$ (START TO EVOKE ALPHA WAVE)

SYSTEM FOR EVOKING ELECTROENCEPHALOGRAM SIGNALS

This is a continuation of application Ser. No. 07/498,671 filed Mar. 26, 1990 now abandoned.

BACKGROUND OF THE INVENTION

1. Field of the Invention

The present invention relates to a system for evoking a desired electroencephalogram signal, e.g., an alpha rhythm, from the brain of a human being to bring the human being into a relaxed condition.

2. Prior Art

It is known in the art that brain waves, i.e., electroencephalogram (EEG) signals, originating in the brain of a human being and the physiological and psychological states of the human being are closely related to each other. For example, when a human being is awake and in an active mental state, beta ($\beta$) rhythms in a frequency range of from about 13 to 30 Hz are dominantly produced. Alpha ($\alpha$) rhythms are prevalent in a relaxed mental state and have a frequency ranging from about 8 to 13 Hz. Brain waves generated during drowsiness and lightsleep are theta ($\theta$) rhythms in a frequency band ranging from about 4 to 7 Hz. The correlation between these brain waves having different frequency ranges and certain human activity phases indicates that the evocation of a certain brain wave through sensory stimulation is apt to put the human being in a corresponding physiological and psychological state.

Based on the analysis of the interaction between the EEG signals and physiological and psychological states, there have heretofore been proposed various systems for evoking alpha waves from the brain of a human being by giving a certain external stimulus to his body, thereby to place him in a physically and psychologically relaxed state for assisting him in lessening stresses and achieving mental concentration.

For example, U.S. Pat. No. 4,315,502 discloses an EEG signal evoking system comprising a pair of goggles having lamps disposed around the lenses, a pair of headphones, and a pulse signal generating means for outputting a predetermined pulse signal to the goggles and headphones. In use, the goggles and headphones are worn by a user, and a pulse signal is applied to the goggles and headphones by the pulse generator. When the lamps on the goggles and the headphones are energized with the pulse signal, external stimulus in the form of flickering light and sound are applied to the user, thus evoking a desired brain wave to bring the user into a relaxed mental state.

With the above conventional EEG signal evoking system, the EEG evoking stimulus signal is artificially generated according to a predetermined pattern irrespective of the nature of the brain waves of the user, and such artificial stimulating pulses are applied to the user for the evocation of the desired EEG rhythm. Therefore, the evoking effect of the known EEG evoking system differs from user to user, and the evoking efficiency of the system is not the same among various users.

SUMMARY OF THE INVENTION

It is an object of the present invention to provide an electroencephalogram signal evoking system for generating a stimulating signal using a brain wave picked up from a user of the system, and feeding back a stimulating light based on the generated stimulating signal to the user for thereby giving a photic stimulus to the user to evoke an electroencephalogram signal with increased efficiency.

It is another object of the present invention to provide an electroencephalogram signal evoking system having a compact structure in which a user can handle it with ease.

According to the present invention, there is provided a system for evoking an electroencephalogram (EEG) signal from the brain of a user, comprising headgear means for being mounted on the head of the user, light-emitting means, mounted on the headgear means, for applying an EEG signal evoking photic stimulus to the eyes of the user; and electrode means, mounted on the headgear means, for detecting brain waves produced by the user, said light-emitting means and electrode means being mounted integrally on said headgear means.

According to the present invention, there is also provided a system for evoking an electroencephalogram (EEG) signal from the brain of a user, comprising a brain wave evoking terminal unit comprising headgear means for being mounted on the head of the user, light-emitting means, mounted on the headgear means, for applying an EEG signal evoking photic stimulus to the eyes of the user, and electrode means, mounted on the headgear means, for detecting brain waves produced by the user, said light-emitting means and electrode means being mounted integrally on said headgear means, the system further comprising a brain wave signal processor, responsive to brain wave signals from the electrode means, for generating a stimulating signal having a frequency corresponding to a brain wave to be evoked, and for applying the stimulating signal to the light-emitting means.

With the above arrangement, since a stimulating signal based on the brain waves of the user himself which are detected by the electrode means is fed back to the user, a biological oscillating circuit having a closed loop including the user himself is established to bring the user rapidly and strongly into a desired brain wave condition.

The brain wave evoking terminal unit and the brain wave signal processor may be separate from each other and electrically connected to each other.

Alternatively, the brain wave signal processor and the brain wave evoking terminal unit may be physically combined into a unitary structure, so that the system is small in size, simple in arrangement, and can be carried and mounted on the user's head with ease.

The above and other objects, features and advantages of the present invention will become more apparent from the following description when taken in conjunction with the accompanying drawings in which preferred embodiments of the present invention are shown by way of illustrative example.

DETAILED DESCRIPTION OF THE PREFERRED EMBODIMENT

Figure 1:
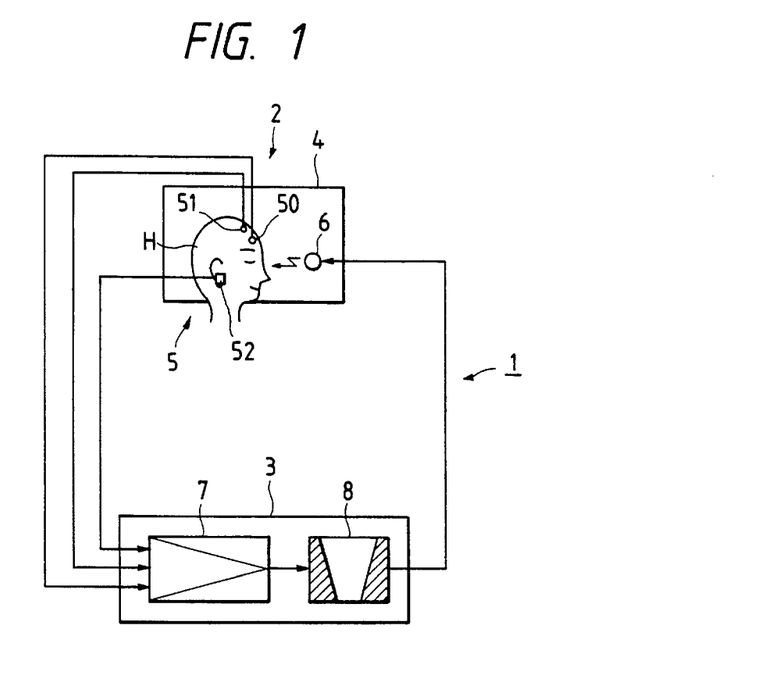
FIG. 1 is a block diagram of a system for evoking an electroencephalogram signal according to a first embodiment of the present invention, the system being shown as being connected to a user.

Like or corresponding parts are denoted by like or corresponding reference characters throughout views.
First Embodiment FIG. 1 shows in block form a system for evoking an electroencephalogram (EEG) signal or a brain wave in accordance with a first embodiment of the present invention.

The EEG signal evoking system, generally designated by the reference numeral 1, includes a brain wave evoking terminal unit 2 to be attached to the head H of a user of the system, and a brain wave signal processor 3 which is electrically connected to the brain wave evoking terminal unit 2. The brain wave evoking terminal unit 2 has output terminals connected to the input terminals of the brain wave signal processor 3, whose output terminal is in turn connected to the input terminal of the brain wave evoking terminal unit 2. Therefore, the brain wave evoking terminal unit 2 and the brain wave signal processor 3 are connected as a closed loop.

The brain wave evoking terminal unit 2 comprises a headset 4 to be attached to the user's head H, a brain wave detecting electrode assembly 5 for detecting EEG signals or brain waves from the user's head H, and a light emitter 6 for applying a photic stimulus signal to the user.

The brain wave detecting electrode assembly 5 comprises a reference electrode 50 to be held against the scalp of the user, a ground electrode 51 also to be held against the scalp of the user, and an indifferent electrode 52 to be normally attached to the lobe of an ear of the user.

The brain wave signal processor 3 comprises a low-noise high-gain biological signal amplifier 7, and a bandpass filter 8 connected to the output terminal of the biological signal amplifier 7. The electrodes 50, 51, 52 of the brain wave detecting electrode assembly 5 are connected to the input terminals of the biological signal amplifier 7. The light emitter 6 is connected to the output terminal of the bandpass filter 8.

Operation of the EEG signal evoking system 1 will be described below. A brain wave of the user is measured as a potential difference between the reference electrode 50 and the ground electrode 51 which are attached to the scalp of the user. The potential of an ear lobe, which is considered to be zero as compared with the potential of the scalp, is detected by the indifferent electrode 52. Signals indicative of the potentials detected by the electrodes 50, 51, 52 are applied to the input terminals of the biological signal amplifier 7.

The biological signal amplifier 7 calculates the potential difference between the reference electrode 50 and the ground electrode 51, and subtracts the potential of the indifferent electrode 52 from the potential difference, thereby producing a brain wave signal with the zero potential used as a reference. Then, the biological signal amplifier 7 applies the brain wave signal to the bandpass filter 8. The brain wave signal normally contains frequency components whose frequency ranges from 1 to 60 Hz.

The bandpass filter 8 receives as an input signal the brain wave signal from the biological signal amplifier 7, extracts and passes only a frequency component corresponding to a brain wave desired to be evoked, while removing the other frequency components. As described above, the brain wave signal contains various frequency components whose frequency ranges from 1 to 60 Hz, the frequency components including an alpha rhythm (8–13 Hz), a beta rhythm (13–30 Hz), and a theta rhythm (4–7 Hz). When the user is in a relaxed mental condition, the frequency component corresponding to the alpha rhythm becomes dominant in the brain wave signal. When the user is awake and in an active metal state, the beta rhythm becomes more intensive, and when the user is asleep, the theta rhythm becomes stronger. Therefore, if only the alpha rhythm of the brain wave signal can be intensified, then the brain of the user can be placed in a relaxed condition. The passband frequency of the bandpass filter 8 can be varied. For example, if the alpha rhythm is to be evoked, the passband frequency is selected to be in the range of from 8 to 13 Hz, if the theta rhythm is to be evoked, the passband frequency is selected to range from 4 to 7 Hz, and if both the alpha rhythm and the theta rhythm are to be evoked, the passband frequency is selected to range from 4 to 13 Hz. Accordingly, only a frequency component which corresponds to the selected passband of the bandpass filter 7 is extracted from the brain wave signal, and is supplied as a stimulating signal to the light emitter 6 on the headset 4.

The light emitter 6 is positioned in front of the eyes of the user. The light emitter 6 generates stimulating light which flickers, in response to the stimulating signal applied to the light emitter 6. The stimulating light, i.e., photic stimulus, is therefore applied to the eyelids of the user who has closed his eyes. When the photic stimulus is applied to the user, a desired brain wave is strongly evoked in the brain of the user. The evoked brain wave is then picked up by the electrode assembly 5 and sent to the biological signal amplifier 7, after which the above photic stimulation is repeated.

Therefore, when the evocation of the certain brain wave is started, a biological oscillating circuit including a closed loop is established by the EEG signal evoking system and the user, and only a signal corresponding to the desired brain wave to be evoked circulates through the closed loop, so that only the desired brain wave is strongly evoked, rapidly bringing the user into a desired evoked EEG condition. As a result, if the desired brain wave is the alpha rhythm, then the user of the system is rapidly induced into a relaxed mental state.

Figure 2:
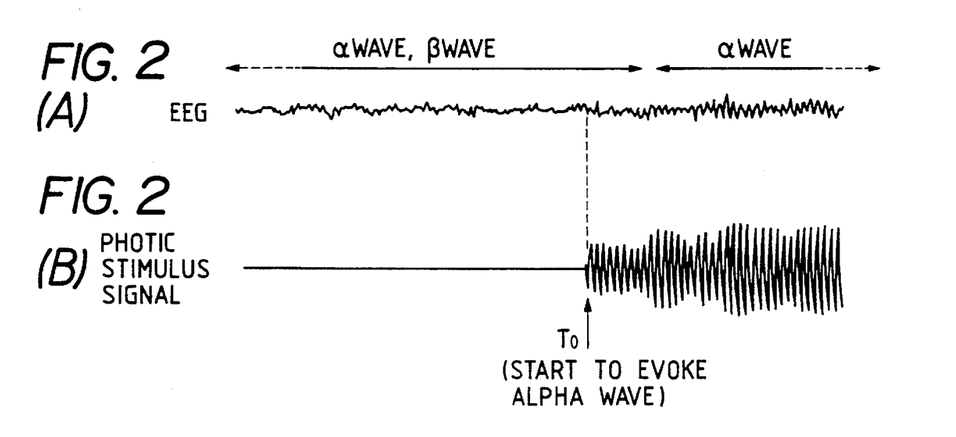
FIG. 2 is a diagram showing a measured alpha wave evoked by the EEG signal evoking system shown in FIG. 1.

FIG. 2 shows the measured waveform of an alpha wave evoked by the EEG signal evoking system shown in FIG. 1. Brain waves picked up by the electrode assembly 5 include alpha and beta rhythms, as indicated at (A) in FIG. 2, whereas a photic stimulus signal applied to the user by the light emitter 6 is indicated at (B) in FIG. 2. When the EEG signal evoking system is switched on at a time $T_o$ to start evoking the alpha rhythm as shown at (B) in FIG. 2, the alpha rhythm in the brain waves is quickly increased in intensity as shown at (A) in FIG. 2.

Second Embodiment

FIGS. 3 through 6 show in block form a system for evoking an EEG signal or a brain wave in accordance with a second embodiment of the present invention.

The EEG signal evoking system, generally designated by the reference numeral 1A, includes a brain wave evoking terminal unit 2A in the form of a pair of goggles to be attached to the head H of a user of the system, a brain wave signal processor 3A, and a battery box 90 serving as a power supply.

The brain wave evoking terminal unit 2A comprises a headband 4A to be attached to the user's head H, brain wave detecting electrodes 50A, 51A, 52A for detecting EEG signals or brain waves from the user's head H, a light emitter 6 for applying a photic stimulus signal to the user, and a light shield 20 for shielding the user's eyes from external light.

Figure 3:
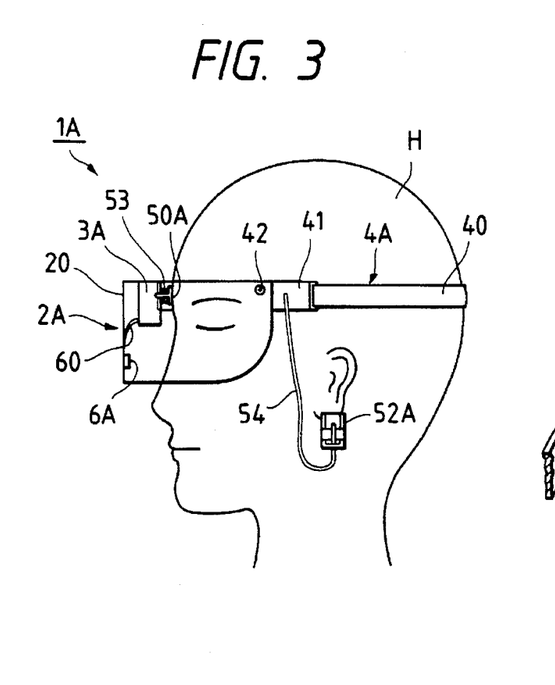
FIG. 3 is a side elevational view, partly seen through, of a system for evoking an electroencephalogram signal according to a second embodiment of the present invention, the system being shown as being attached to the head of a user.

As shown in FIG. 3, the headband 4A has a belt 40 made of an elastic material such as rubber and a holder 41 made of a harder material such as plastic. The holder 41 is in the shape of a horseshoe so as to extend along the forehead of the user's head H. The belt 40 is connected to the opposite ends of the holder 41 and extends along the lateral sides of the head H and around the rear side of the head H. Since the belt 40 is elastic, the headband 4A can easily be attached to and removed from the head H when the belt 40 is stretched. The belt 40 may be in the form of a waistband for easy attachment to and removal from the head H.

Figure 4:
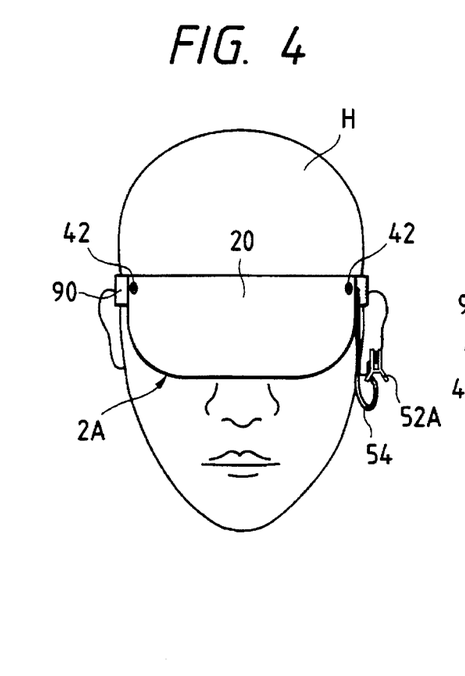
FIG. 4 is a front elevational view of the EEG signal evoking system shown in FIG. 3.
Figure 5:
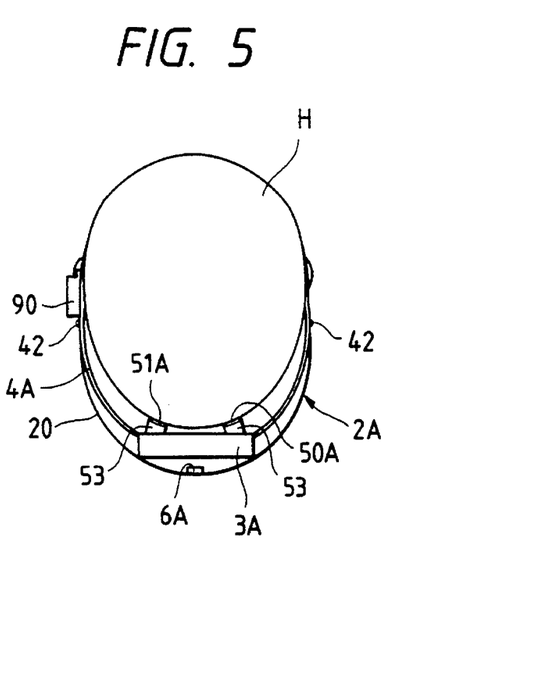
FIG. 5 is a plan view of the EEG signal evoking system illustrated in FIG. 3.

As illustrated in FIGS. 3 and 4, the light shield 20, which is black in color and made of a material such as vinyl chloride or the like, is disposed in front of the face of the user so as to cover the eyes. The light shield 20 has side ends fixed to the holder 41 by means of screws 42. As shown in FIGS. 3 and 5, the brain wave signal processor 3A which is housed in a plastic case or the like is fixed to the central portion of the holder 41 over the face of the user. The electrodes 50A, 51A, which are reference and ground electrodes, respectively, in the form of buttons, are mounted on an inner peripheral wall of the brain wave signal processor 3A. When the brain wave evoking terminal unit 2A is worn by the user, the electrodes 50A, 51A are held against laterally spaced areas of the forehead user for picking up brain waves from the forehead. These electrodes 50A, 51A are electrically connected to the brain wave signal processor 3A.

Figure 6:
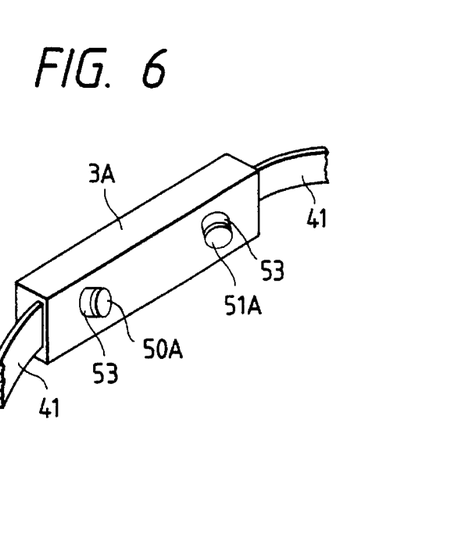
FIG. 6 is a perspective view of an EEG signal processor and EEG signal detecting electrodes of the EEG signal evoking system shown in FIG. 3.

As shown in FIG. 6, the reference electrode 50A and the ground electrode 51A are attached to the inner peripheral wall of the brain wave signal processor 3A through respective cushioning members 53 which are made of an elastic spongy material. Therefore, the reference electrode 50A and the ground electrode 51A are flexibly and elastically displaceable laterally and back and forth with respect to the brain wave signal processor 3A. As a result, when the brain wave evoking terminal unit 2A is mounted on the user's head H, the head H is protected from injury and the electrodes 50A, 51A are softly held against the forehead of the user naturally along the curved surface of the forehead.

As shown in FIGS. 3 and 5, a light emitter 6A which comprises a light-emitting diode (LED) or the like for emitting a photic stimulus is attached to the inner surface of the light shield 20. The light emitter 6A is positioned within the visual field of the user, i.e., on the inner surface of the light shield 20 near the lower end thereof. The light emitter 6A is electrically connected to the brain wave signal processor 3A through a cable 60. The light emitter 6A is supplied with a photic stimulus signal for evoking an EEG signal or a brain wave from the brain wave signal processor 3A. As shown in FIGS. 3 and 4, the indifferent electrode 52A which is in the form of a clip for being attached to the left ear of the user is electrically connected to the brain wave signal processor 3A through a cable 54 which extends through the holder 41.

As illustrated in FIGS. 4 and 5, the battery box 90 for supplying electric energy to various components of the EEG signal evoking system is electrically coupled to the brain wave signal processor 3A through a cable (not shown) extending through the holder 41.

The brain wave signal generator 3A is of the same construction as that of the brain wave signal generator 3 shown in FIG. 1.

The EEG signal evoking system thus constructed is small in size, can be handled with ease, and portable.

The EEG signal evoking system of the second embodiment is used as follows: It is assumed that the EEG signal evoking system is used to evoke an alpha rhythm, and hence the bandpass filter of the brain wave signal processor 3A is arranged to have a passband frequency in the range of from 8 to 13 Hz.

The user of the EEG signal evoking system takes a relaxed posture on a reclining chair, for example, and wears brain wave evoking terminal unit 2A on the head H while stretching the belt 40 of the headband 4A. The eyes of the user are automatically covered with the light shield 20, so that they will shielded from external light. The indifferent electrode 52A is clipped on the lobe of the left ear. At the same time that the brain wave evoking terminal unit 2A is mounted on the head H, the reference electrode 50A and the ground electrode 51A are automatically held against laterally spaced areas of the forehead of the user.

After the brain wave evoking terminal unit 2A has been installed, the user closes his eyes and turns on the power supply to start evoking the brain wave.

When the brain wave evoking process is started, brain waves are picked up by the electrodes 50A, 51A held against the forehead of the user. The picked-up brain wave signals are sent to the biological signal amplifier (not shown) of the brain wave signal processor 3A and amplified to a predetermined level thereby. The amplified brain wave signals are then set to the bandpass filter, which extracts a frequency component in the range of from 8 to 13 Hz, which corresponds to the alpha rhythm, from the brain wave signals. The extracted frequency signal is then transmitted as a stimulating signal to the light emitter 6A.

In response to the stimulating signal corresponding to the alpha rhythm from the bandpass filter, the light emitter 6 generates stimulating light which flickers. The stimulating light, i.e., photic stimulus, is therefore applied to the eyelids of the user who has closed his eyes. When the photic stimulus is applied to the user, a desired brain wave is strongly evoked in the brain of the user. The evoked brain wave is then picked up by the electrodes 50A, 51A, 52A and sent to the biological signal amplifier of the brain wave signal processor 3A, after which the above photic stimulation is repeated. Therefore, when the evocation of the certain brain wave is started, a biological oscillating circuit including a closed loop is established by the EEG signal evoking system and the user, and only a signal corresponding to the desired brain wave to be evoked circulates through the closed loop, so that only the alpha rhythm is strongly evoked, rapidly bringing the user into a desired evoked EEG condition.

In the second embodiment, the battery box 90 may be disposed in any other position than illustrated on the brain wave evoking terminal unit 2A, and the indifferent electrode 52A may be attached to the lobe of the right ear.

The battery box 90 may be dispensed with if a power supply battery is housed in the brain wave signal processor 3A itself. The brain wave signal processor 3A and the battery box 90 may be separate from the brain wave evoking terminal unit 2A and may be either placed on one side of the user or attached to the waistband of the user. Rather than attaching the ground electrode 51A to the forehead of the user, it may be in the form of a ring electrode made of electrically conductive rubber and fitted over a fingertip or a wrist of the user.

Third Embodiment

Figure 7:
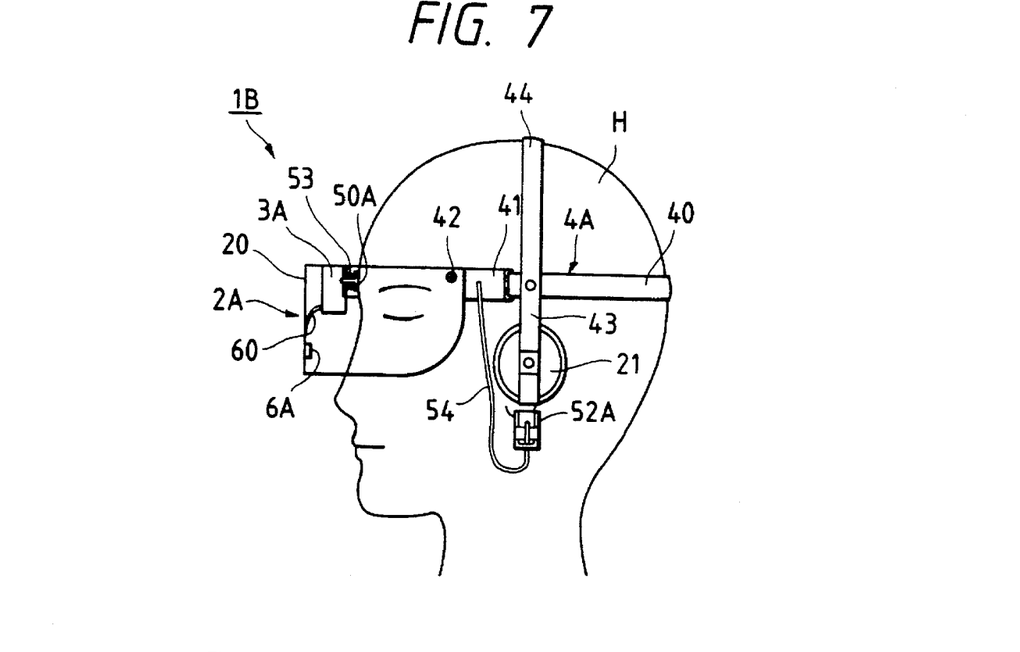
FIG. 7 is a side elevational view, partly seen through, of a system for evoking an electroencephalogram signal according to a third embodiment of the present invention, the system being shown as being attached to the head of a user.
Figure 8:
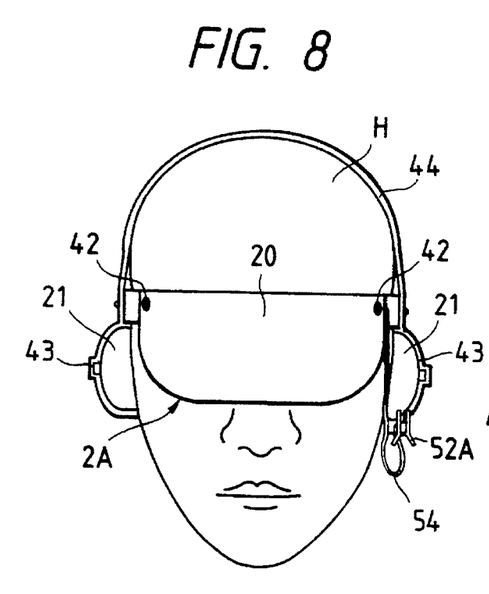
FIG. 8 is a front elevational view of the EEG signal evoking system shown in FIG. 7.
Figure 9:
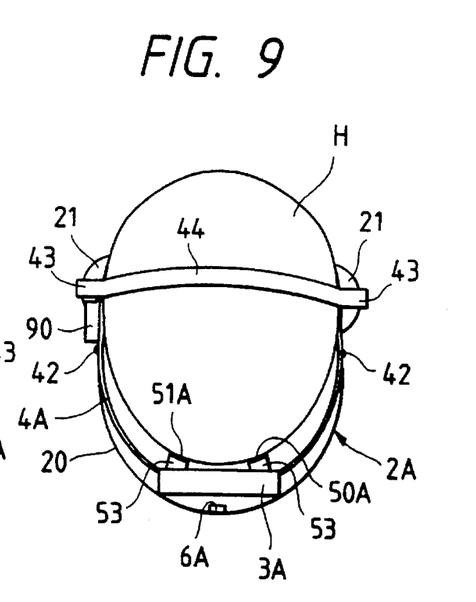
FIG. 9 is a plan view of the EEG signal evoking system illustrated in FIG. 7.

An EEG signal evoking system according to a third embodiment shown in FIGS. 7 through 9 is designed for making the user concentrate on flickering stimulating light emitted by the light emitter 6A for a greater EEG evoking effect.

The EEG signal evoking system, generally denoted at 1B in FIGS. 7 through 9, comprises a brain wave evoking terminal unit 2A, which is identical to the brain wave evoking terminal unit 1A of the second embodiment, a pair of ear covers or sound shields 21, and a pair of ear cover attachments 43 on which the ear covers 21 are supported.

With the arrangement shown in FIGS. 7 through 9, since any noise from external sources is shut out or attenuated by the ear covers 21, the user can mentally concentrate on the flickering light from the light emitter 6A for a higher EEG evoking effect. To prevent the belt 40 from being lowered by the weight of the ear covers 21 and the attachments 43, and also to allow the brain wave evoking terminal unit 2A to be attached and detached easily, the belt 40 may be combined with an auxiliary belt 44 which extends vertically around the head H and is joined to the belt 40 and the attachments 43. Instead of the ear covers 21, ear plugs for insertion into the ears may be used for shutting out noise.

Fourth Embodiment

FIGS. 10 through 13 show an EEG signal evoking system according to a fourth embodiment of the present invention.

Figure 10:
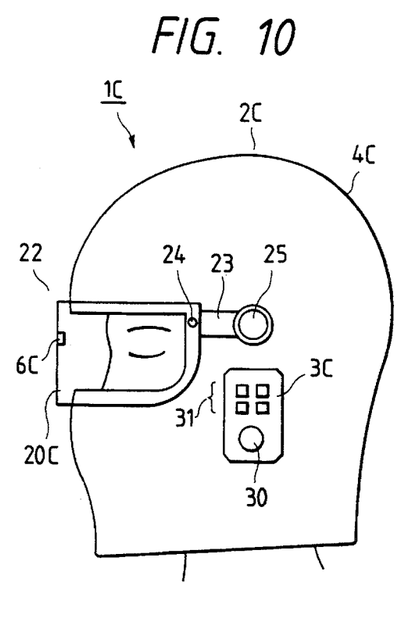
FIG. 10 is a side elevational view, partly seen through, of a system for evoking an electroencephalogram signal according to a fourth embodiment of the present invention, the system being shown as being attached to the head of a user.

The EEG signal evoking system, generally indicated by 1C in FIG. 10, has a brain wave evoking terminal unit 2C in the shape of a helmet which can be mounted on the head H of a user, and a brain wave signal processor 3C attached to the brain wave evoking terminal unit 2C. A battery box as a power supply is housed in the brain wave signal processor 3C.

The brain wave evoking terminal unit 2C comprises a head cover 4C to be mounted on the head H, brain wave detecting electrodes 50C, 51C, 52C, a light emitter 6C for generating a photic stimulus, a light shield 22, and a pair of ear pads or sound shields 21C.

Figure 11:
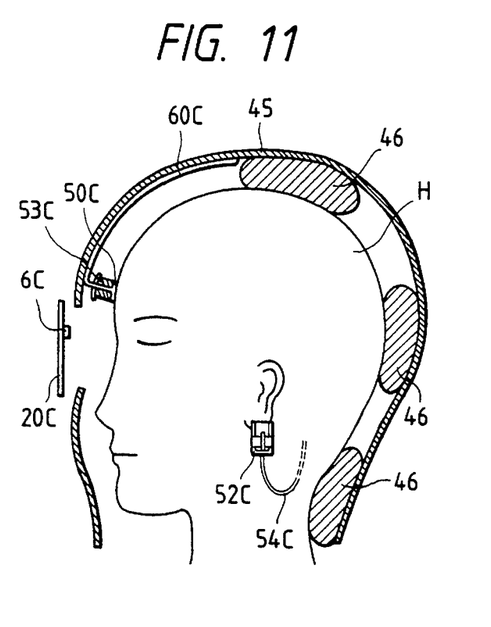
FIG. 11 is a sectional side elevational view of the EEG signal evoking system shown in FIG. 10.
Figure 12:
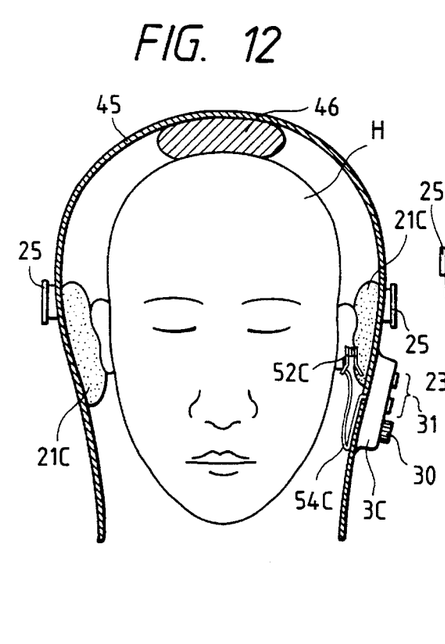
FIG. 12 is a sectional front elevational view of the EEG signal evoking system shown in FIG. 10.

As shown in FIG. 11, the head cover 4C has an outer shell 45 made of any of various materials such as plastic, metal, etc., and a pad member 46 made of a soft material such as sponge. The pad member 46 serves to hold the outer shell 45 in position on the head H, and protects the head H from shocks.

Figure 13:
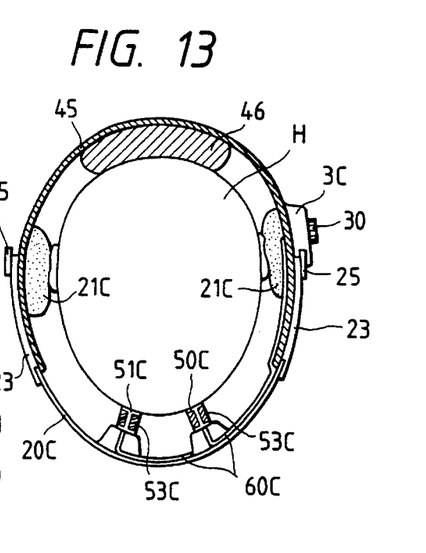
FIG. 13 is a sectional plan view of the EEG signal evoking system illustrated in FIG. 10.

As shown in FIGS. 10, 11, and 13, the outer shell 45 has an opening defined therein in front of the eyes of the user, and the light shield 22 is attached to the outer shell 45 in covering relation to the opening. The light shield 22 has a light shield panel 20C and a pair of laterally spaced attachment arms 23. The opposite ends of the light shield panel 20C are fixed to the attachment arms 23 by screws 24. The attachment arms 23 are mounted on respective pivots 25 on lateral sides of the head cover 4C for angular movement about the pivots 25. Therefore, the light shield 20C can be moved between a lower position in which it covers the opening in the head cover 4C and an upper position in which it uncovers the opening.

The light emitter 6C, which may comprise an LED or the like, is mounted on the inner surface of the light shield panel 20C within the visual field of the user.

The reference electrode 50C and the ground electrode 51C, which are in the shape of buttons, are attached to the inner surface of the outer shell 45 so as to be held against laterally spaced areas of the forehead of the user. These electrodes 50C, 51C are attached to the outer shell 45 through respective cushioning members 53C of a spongy material, as with the second and third embodiments.

The brain wave signal processor 3C, which is housed in a case made of plastic, metal, or the like, is integrally attached to the outer surface of the outer shell 45 in the vicinity of the left ear of the user. The brain wave signal processor 3C has a signal level adjusting knob 30 and various control switches 31 (such as a selector switch for selecting a brain wave to be evoked), and accommodates the battery box (not shown) therein. The brain wave signal processor 3C has input terminals to which the reference electrode 50C and the ground electrode 51C are connected through cables 60C. The output terminal of the brain wave signal processor 3C is connected to the light emitter 6C through a cable (not shown).

The indifferent electrode 52C in the form of a clip to be attached to the left ear of the user is disposed within the outer shell 45 inwardly of the brain wave signal processor 3C, and is connected to the brain wave signal processor 3C through a cable 54C.

The EEG signal evoking system 1C of the above construction allows the user to concentrate on the photic stimulus generated by the light emitter 6C for better brain wave evocation because his head is enclosed in the helmet-shaped terminal unit 2C in use. The ear pads 21C, which are made of a spongy material, are attached to the inner surface of the outer shell 45 for covering the ears of the user to shut off noise. The EEG signal evoking system 1C is better in blocking off external light and noise for higher brain wave revocation.

Fifth Embodiment

Figure 14:
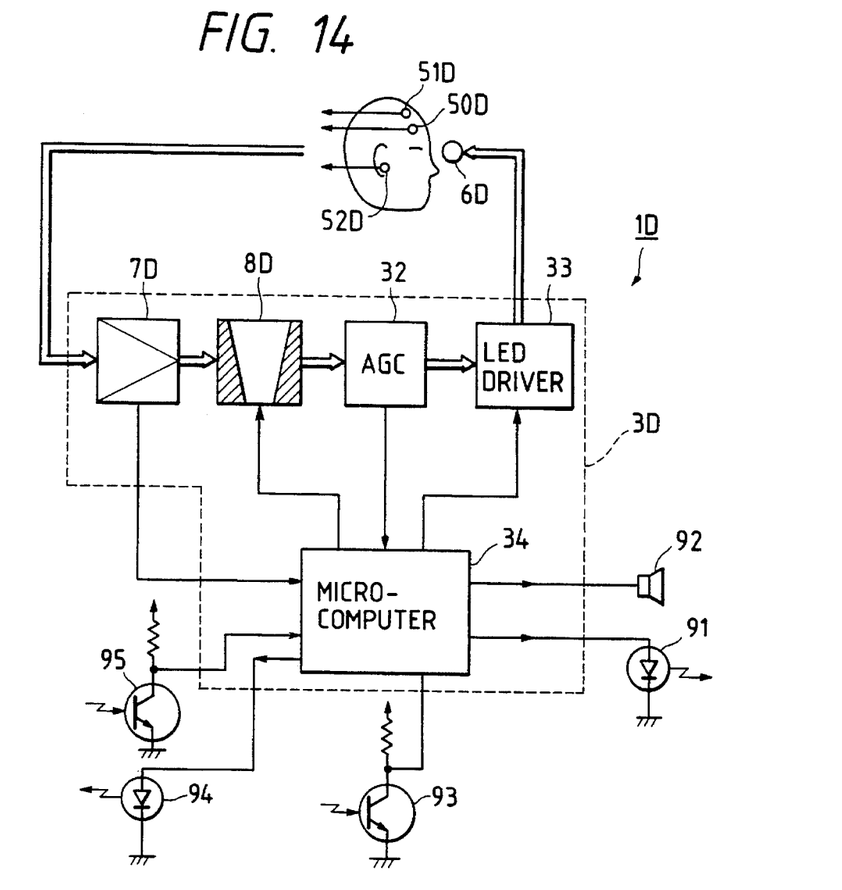
FIG. 14 is a block diagram of a system for evoking an electroencephalogram signal according to a fifth embodiment of the present invention, the system being shown as being connected to a user.

An EEG signal evoking system according to a fifth embodiment has a brain wave signal processor shown in FIG. 14.

The brain wave signal processor, generally denoted at 3D, of the EEG signal evoking system 1D includes a biological signal amplifier 7D, a bandpass filter 8D connected to the output terminal of the biological signal amplifier 7D, an automatic gain control (AGC) circuit 32 connected to the output terminal of the bandpass filter 8D, and an LED driver 33 connected to the output terminal of the AGC circuit 32. The output terminal of the LED driver 33 is connected to a light emitter 6D. The brain wave signal processor 3D also includes a microcomputer 34 which is connected to the biological signal amplifier 7D, the bandpass filter 8D, the AGC circuit 32, and the LED driver 33.

The AGC circuit 32 serves to keep the stimulating signal at a constant level so that any fluctuation in the amplitude of a photic signal emitted by the light emitter 6D will be minimized. The LED driver 33 effects voltage-current conversion on the output signal from the AGC circuit 32 to drive the light emitter 6D for light modulation.

The microcomputer 34 controls the operation of the above various components of the brain wave signal processor 3D. More specifically, the microcomputer 34 monitors the output signal from the biological signal amplifier 7D. When the level of the output signal from the biological signal amplifier 7D exceeds a certain reference level, the microcomputer 34 judges the output signal as a noise. At this time, the microcomputer 34 energizes the LED of an indicator 91 which is either on the terminal unit worn by the user or separate from the terminal unit, or energizes a speaker 92, or changes the interval at which the light emitted by the light emitter 6D flickers, or continuously energizes or deenergizes the light emitter 6D. More specifically, the brain wave signals are of a very weak intensity with the frequency ranging from 4 to 30 Hz. If the level of signals picked up by the electrodes 50D, 51D, 52D is excessively high or the frequency thereof is too high, it is determined by the microcomputer 34 that the picked-up signals are signals other than the brain wave signals, e.g., a ham noise introduced from the commercial power supply.

A photoelectric device 93 such as a Cds or a phototransistor is connected, as a light sensor for detecting ambient light, to the microcomputer 34 for controlling the LED driver 33, so that the brightness of the photic stimulus can be varied depending on the ambient brightness. If the ambient brightness is low, the brightness of the photic stimulus is lowered, and if the ambient brightness is high, the brightness of the photic stimulus is increased.

The brain wave signals and other data may be transmitted from the microcomputer 34, through a wireless transmitter or an infrared signal transmitter which has a light emitter 94 such as an LED, to a data processing system (not shown) for recording or evaluating the data. A light detector 95 such as a phototransistor for receiving control signals is connected to the microcomputer 34 to remotely control the brightness of the photic stimulus, the level of the light modulation, and the passband of the bandpass filter 8D.

The microcomputer 34 may also be programmed to provide various other functions. For example, it may have a timer function to energize the light emitter 6D at a preset time or energize an indicator or a buzzer to indicate the arrival of a preset time. The microcomputer 34 may also have an automatic power-off function for automatically turning off the power supply after elapse of a preset time if the user falls asleep. Furthermore, the microcomputer 34 may have a power supply monitor function for monitoring the voltage of the battery in the battery box and indicating a battery power shortage in advance.

Sixth Embodiment

Figure 15:
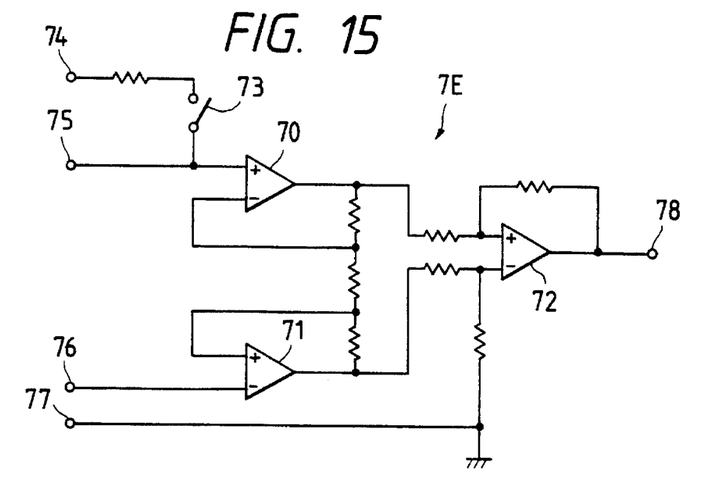
FIG. 15 is a circuit diagram, partly in block form, of a biological signal amplifier of a system for evoking an electroencephalogram signal according to a sixth embodiment of the present invention.

FIG. 15 shows a biological signal amplifier of an EEG signal evoking system according to a sixth embodiment of the present invention. The biological signal amplifier, generally indicated at 7E, includes buffer amplifiers 70, 71, a differential amplifier 72, a switch 73 for detecting an electrode contact failure, and terminals 74 through 78.

The terminal 74 is connected to the switch 73. The terminal 75 is connected to a reference electrode (not shown). The terminal 76 is connected to an indifferent electrode (not shown). The terminal 77 is connected to a ground electrode (not shown). The terminal 78 is connected to a bandpass filter (not shown). Brain wave signals supplied through the terminals 75, 76 are adjusted by the respective buffer amplifiers 70, 71. Then, the potential of the scalp of the user is subtracted by the differential amplifier 72, which produces a signal with the zero potential of the indifferent electrode being used as a reference.

The switch 73 serves to determine whether the reference electrode and the ground electrode are held in good electric contact with the scalp of the user or not. Before an EEG signal evoking process is started, the switch 73 is turned on in a predetermined period of time so that an AC signal having a frequency of about 10 Hz, analogous to a brain wave signal, is supplied from an oscillator (not shown) through the terminal 74 and the switch 73 to the buffer amplifier 70. The electric contact made by the reference electrode and the ground electrode can then be checked depending on the level of the output signal produced in response to the AC signal of 10 Hz. More specifically, if the reference and ground electrodes are held in good contact with the forehead of the user, then the impedance between these electrodes is small, and the AC signal of 10 Hz supplied through the switch 73 flows through a short circuit between the electrodes. Therefore, the output signal of 10 Hz from the differential amplifier 72 is slow in level. If the differential and ground electrodes are not held in good contact with the forehead of the user, then the impedance between these electrodes is high, and the AC signal of 10 Hz is applied almost in its entirety to the differential amplifier 72 through the switch 73. Consequently, the output signal of 10 Hz from the differential amplifier 72 is high in level. Some monitoring system using a microcomputer or the like which monitors the level of the output signal of 10 Hz can thus detect any contact failure of the reference electrode and the ground electrode prior to the starting of an EGG signal revoking process. After the above monitoring and checking process is finished, the switch 73 is opened, i,e., turned off.

Although there have been described what are at present considered to be the preferred embodiments of the present invention, it will be understood that the invention may be embodies in other specific forms without departing from the essential characteristics thereof. The present embodiments are therefore to be considered in all aspects as illustrative, and not restrictive. The scope of the invention is indicated by the appended claims rather than by the foregoing description.

What is claimed is:

1. A system for evoking a desired electroencephalogram (EEG) signal from the brain of a user by feeding back a detected brain wave component to the user, the system comprising:

means for evoking the desired EEG signal, said evoking means comprising:

headgear means for being mounted on the head of the user;

light-emitting means for applying an EEG signal evoking photic stimulus to the eyes of the user;

electrode means for detecting brain waves produced by the user;

light shield means, mounted on said headgear means so as not to contact a user's face, for covering the user's eyes, thereby shielding the eyes from external light; and signal processing means for extracting, from the detected brain waves, only that brain wave having a frequency which is equal to a frequency of the desired EEG signal;

said electrode means being integrally mounted on said headgear means so as to automatically abut in a desired position against the scalp of the user to detect the brain wave of the user when said headgear means is mounted on the user's head, said EEG signal evoking photic stimulus being a user stimulating light which flickers at the frequency of the brain wave extracted by said signal processing means, and said light-emitting means being mounted on said light shield means so as to face the user and so as to be positioned within the user's visual field, further comprising a light sensor for detecting ambient brightness, and means for varying a brightness of the photic stimulus depending on the ambient brightness detected by the light sensor.

2. A system for evoking a desired electroencephalogram (EEG) signal from the brain of a user, the system comprising:

means for evoking the desired EEG signal, said evoking means comprising:

a brain wave evoking terminal unit comprising headgear means for being mounted on the head of the user, light-emitting means, mounted on said headgear means, for applying an EEG signal evoking photic stimulus to the eyes of the user, electrode means, mounted on said headgear means, for detecting brain waves produced by the user, and light shield means, mounted on said headgear means so as not to contact the user's face, for covering the user's eyes, thereby shielding the user's eyes from external light, said electrode means being mounted integrally on said headgear means so as to automatically abut in a desired position against the scalp of the user to detect the brain wave of the user when said headgear means is mounted on the user's head, and said light-emitting means being mounted on said light shield means so as to face the user and so as to be positioned within the user's visual field; and a brain wave signal processor, responsive to brain wave signals from said electrode means, for generating a stimulating signal having a frequency corresponding only to the desired EEG signal, and for applying the generated stimulating signal to said light-emitting means, wherein said brain wave signal processor comprises a light sensor for detecting ambient brightness, and means for controlling a level of the stimulating signal depending on the ambient brightness detected by the light sensor.

3. A system for evoking a desired electroencephalogram (EEG) signal from the brain of a user by feeding back a detected brain wave component to the user, the system comprising:

headgear means for being mounted on the head of the user;

electrode means for detecting brain waves produced by the user, said brain wave including a plurality of target EEG signals;

light shield means, mounted on said headgear means so as not to contact the user's face, for covering the user's eyes, thereby shielding the user's eyes from external light;

signal processing means for extracting at least one of the target EEG signals from the brain waves detected by the electrode means; and light-emitting means for receiving the EEG signals extracted by the signal processing means and applying an EEG signal evoking photic stimulus to the eyes of the user, said electrode means being integrally mounted on said headgear means so as to automatically abut in a desired position against the scalp of the user to detect the brain wave of the user when the headgear means is mounted on the user's head, said EEG signal evoking photic stimulus being a user stimulating light which flickers at a frequency of the target EEG signals extracted by said signal processing means, and said light-emitting means being mounted on said light shield means so as to face the user and so as to be positioned within the user's visual field, further comprising a light sensor for detecting ambient brightness, and means for varying a brightness of the photic stimulus depending on the ambient brightness detected by the light sensor.

4. A system for evoking a desired electroencephalogram (EEG) signal from the brain of a user, comprising:

a brain wave evoking terminal unit comprising headgear means for being mounted on the head of the user, electrode means, mounted on said headgear means, for detecting brain waves produced by the user, light shield means, mounted on said headgear means so as not to contact the user's face, for covering the user's eyes, thereby shielding the user's eyes from external light and light-emitting means for receiving a stimulating signal and applying an EEG signal evoking photic stimulus to the eyes of the user, said electrode means being integrally mounted on said headgear means so as to automatically abut in a desired position against the scalp of the user to detect the brain wave of the user when the headgear means is mounted on the user's head, said brain wave including a plurality of target EEG signals, and said light-emitting means being mounted on said light shield means so as to face the user and so as to be positioned within the user's visual field; and a brain wave signal processor comprising extracting means for extracting at least one of the target EEG signals from the brain waves detected by the electrode means, and means for generating a stimulating signal having a frequency of the EEG signals extracted by the extracting means, and for applying the stimulating signal to said light-emitting means, said EEG signal evoking photic stimulus being a user stimulating light which flickers at a frequency of the target EEG signals extracted by said signal processing means, wherein said brain wave signal processor comprises a light sensor for detecting ambient brightness, and means for controlling a level of the stimulating signal depending on the ambient brightness detected by the light sensor.

5. A system for evoking a desired electroencephalogram (EEG) signal from the brain of a user, the system comprising:

headgear means for being mounted on the head of the user;

light-emitting means for applying an EEG signal evoking photic stimulus to the eyes of the user; and light shield means, mounted on said headgear means so as not to contact the user's face, for covering the user's eyes, thereby shielding the user's eyes from external light;

electrode means for detecting brain waves produced by the user, wherein said electrode means are integrally mounted on said headgear means so as to automatically abut in a desired position against the scalp of the user to detect the brain wave of the user when the headgear means is mounted on the user's head, and said light-emitting means is mounted on said light shield means so as to face the user and so as to be positioned within the user's visual field, further comprising a light sensor for detecting ambient brightness, and means for varying a brightness of the photic stimulus depending on the ambient brightness detected by the light sensor.

* * * * *